United States Patent
Song et al.

(10) Patent No.: US 6,172,231 B1
(45) Date of Patent: Jan. 9, 2001

(54) OXIDATION PROCESS USING PERIODIC ACID

(75) Inventors: Zhiguo Song; Mangzu Zhao, both of Edison; David M. Tschaen, Holmdel, all of NJ (US)

(73) Assignee: Merck & Co., Inc., Rahway, NJ (US)

( * ) Notice: Under 35 U.S.C. 154(b), the term of this patent shall be extended for 0 days.

(21) Appl. No.: 09/283,465

(22) Filed: Apr. 1, 1999

Related U.S. Application Data

(60) Provisional application No. 60/081,446, filed on Apr. 9, 1998, now abandoned.

(51) Int. Cl.$^7$ .................. C07D 221/04; C07D 405/04
(52) U.S. Cl. .............................. 546/112; 546/183
(58) Field of Search ...................... 546/112, 183

(56) References Cited

U.S. PATENT DOCUMENTS 5,962,688  *  10/1999  Devine et al. ............... 546/112

* cited by examiner

Primary Examiner—Charanji S. Aulakh

(74) Attorney, Agent, or Firm—Valeri J. Camara; Mark R. Daniel

(57) ABSTRACT

The present invention relates to a periodic acid oxidation which converts the penultimate intermediate bearing a primary alcohol to the target endothelin antagonist compound of Formula I having a carboxylic acid.

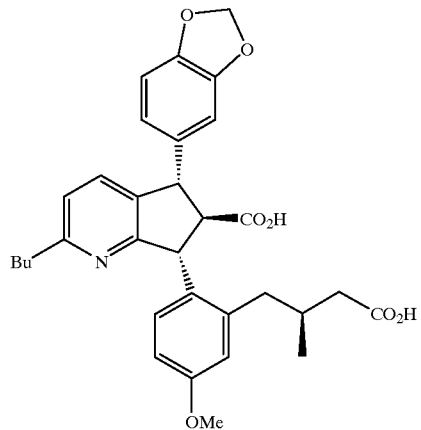

12 Claims, No Drawings

OXIDATION PROCESS USING PERIODIC ACID

This non-provisional application claims priority from provisional application U.S.S.No. 60/081,446, filed Apr. 9, 1998 (now abandoned).

BACKGROUND OF THE INVENTION

The present invention relates to an oxidation process which converts the penultimate intermediate to the target endothelin antagonist compound. This oxidation method avoids the disposal issues associated with running a Jones oxidation reaction, as well as reducing the epimerization of any α-chiral centers and is a one step procedure.

The endothelin antagonist compound possessing a high affinity for at least one of two receptor subtypes, are responsible for the dilation of smooth muscle, such as blood vessels or in the trachea. The endothelin antagonist compounds provide a potentially new therapeutic target, particularly for the treatment of hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, restenosis, prostatauxe endotoxin shock, endotoxin-induced multiple organ failure or disseminated intravascular coagulation, and/or cyclosporin-induced renal failure or hypertension.

Endothelin is a polypeptide composed of amino acids, and it is produced by vascular endothelial cells of human or pig. Endothelin has a potent vasoconstrictor effect and a sustained and potent pressor action (Nature, 332, 411–415 (1988)).

Three endothelin isopeptides (endothelin-1, endothelin-2 and endothelin-3), which resemble one another in structure, exist in the bodies of animals including human, and these peptides have vasoconstriction and pressor effects (Proc. Natl. Acad, Sci, U.S.A., 86, 2863–2867 (1989)).

As reported, the endothelin levels are clearly elevated in the blood of patients with essential hypertension, acute myocardial infarction, pulmonary hypertension, Raynaud's disease, diabetes or atherosclerosis, or in the washing fluids of the respiratory tract or the blood of patients with asthmaticus as compared with normal levels (Japan, J. Hypertension, 12, 79, (1989), J. Vascular medicine Biology, 2, 207 (1990), Diabetologia, 33, 306–310 (1990), J. Am. Med. Association, 264, 2868 (1990), and The Lancet, ii, 747–748 (1989) and ii, 1144–1147 (1990)).

Further, an increased sensitivity of the cerebral blood vessel to endothelin in an experimental model of cerebral vasospasm (Japan. Soc. Cereb. Blood Flow & Metabol., 1, 73 (1989)), an improved renal function by the endothelin antibody in an acute renal failure model (J. Clin, invest., 83, 1762–1767 (1989), and inhibition of gastric ulcer development with an endothelin antibody in a gastric ulcer model (Extract of Japanese Society of Experimental Gastric Ulcer, 50 (1991)) have been reported. Therefore, endothelin is assumed to be one of the mediators causing acute renal failure or cerebral vasospasm following subarachnoid hemorrhage.

Further, endothelin is secreted not only by endothelial cells but also by tracheal epithelial cells or by kidney cells (FEBS Letters, 255, 129–132 (1989), and FEBS Letters, 249, 42–46 (1989)).

Endothelin was also found to control the release of physiologically active endogenous substances such as renin, atrial natriuretic peptide, endothelium-derived relaxing factor (EDRF), thromboxane $A_2$, prostacyclin, noradrenaline, angiotensin II and substance P (Biochem. Biophys, Res. Commun., 157, 1164–1168 (1988); Biochem. Biophys, Res. Commun., 155, 20 167–172 (1989); Proc. Natl. Acad. Sci. U.S.A., 85 1 9797–9800 (1989); J. Cardiovasc. Pharmacol., 13, S89–S92 (1989); Japan. J. Hypertension, 12, 76 (1989) and Neuroscience Letters, 102, 179–184 (1989)). Further, endothelin causes contraction of the smooth muscle of gastrointestinal tract and the uterine smooth muscle (FEBS Letters, 247, 337–340 (1989); Eur. J. Pharmacol., 154, 227–228 (1988); and Biochem. Biophys Res. Commun., 159, 317–323 (1989)). Further, endothelin was found to promote proliferation of rat vascular smooth muscle cells, suggesting a possible relevance to the arterial hypertrophy (Atherosclerosis, 78, 225–228 (1989)). Furthermore, since the endothelin receptors are present in a high density not only in the peripheral tissues but also in the central nervous system, and the cerebral administration of endothelin induces a behavioral change in animals, endothelin is likely to play an important role for controlling nervous functions (Neuroscience Letters, 97, 276–279 (1989)).

Particularly, endothelin is suggested to be one of mediators for pain (Life Sciences, 49, PL61–PL65 (1991)).

Internal hyperplastic response was induced by rat carotid artery balloon endothelial denudation. Endothelin causes a significant worsening of the internal hyperplasia (J. Cardiovasc. Pharmacol., 22, 355–359 & 371–373(1993)). These data support a role of endothelin in the phathogenesis of vascular restenosis. Recently, it has been reported that both ETA and ETB receptors exist in the human prostate and endothelin produces a potent contraction of it. These results suggest the possibility that endothelin is involved in the pathophysiology of benign prostatic hyperplasia (J. Urology, 151, 763–766(1994), Molecular Pharmocol., 45, 306–311 (1994)).

On the other hand, endotoxin is one of potential candidates to promote the release of endothelin. Remarkable elevation of the endothelin levels in the blood or in the culture supernatant of endothelial cells was observed when endotoxin was exogenously administered to animals or added to the culture endothelial cells, respectively. These findings suggest that endothelin is an important mediator for endotoxin-induced diseases (Biochem. Biophys. Commun., 161, 1220–1227 (1989); and Acta Physiol. Scand., 137, 317–318(1989)).

Further, it was reported that cyclosporin remarkably increased endothelin secretion in the renal cell culture (LLC-PKL cells) (Eur. J. Pharmacol., 180, 191–192 (1990)). Further, dosing of cyclosporin to rats reduced the glomerular filtration rate and increased the blood pressure in association with a remarkable increase in the circulating endothelin level. This cyclosporin-inducea renal failure can be suppressed by the administration of endothelin antibody (Kidney Int., 37, 1487–1491 (1990)). Thus, it is assumed that endothelin is significantly involved in the pathogenesis of the cyclosporin-induced diseases.

Such various effects of endothelin are caused by the binding of endothelin to endothelin receptors widely distributed in many tissues (Am. J. Physiol., 256, R856–R866 (1989)).

It is known that vasoconstriction by the endothelins is caused via at least two subtypes of endothelin receptors (J. Cardiovasc. Pharmacol., 17(Suppl.7), S119–SI21 (1991)). One of the endothelin receptors is $ET_A$ receptor Selective to ET-1 rather than ET-3, and the other is $ET_B$ receptor equally active to ET-1 and ET-3. These receptor proteins are reported to be different from each other (Nature, 348, 730–735 (1990)).

These two subtypes of endothelin receptors are differently distributed in tissues. It is known that the $ET_A$ receptor is present mainly in cardiovascular tissues, whereas the $ET_B$ receptor is widely distributed in various tissues such as brain, kidney, lung, heart and vascular tissues.

Substances which specifically inhibit the binding of endothelin to the endothelin receptors are believed to antagonize various pharmacological activities of endothelin and to be useful as a drug in a wide field. Since the action of the endothelins is caused via not only the $ET_A$ receptor but also the $ET_B$ receptor, novel non-peptidic substances with ET receptor antagonistic activity to either receptor subtype are desired to block activities of the endothelins effectively in various diseases.

Endothelin is an endogenous substance which directly or indirectly (by controlling liberation of various endogenous substances) induces sustained contraction or relaxation of vascular or non-vascular smooth muscles, and its excess production or excess secretion is believed to be one of pathogeneses for hypertension, pulmonary hypertension, Raynaud's disease, bronchial asthma, gastric ulcer, diabetes, arteriosclerosis, restenosis, acute renal failure, myocardial infarction, angina pectoris, cerebral vasospasm and cerebral infarction. Further, it is suggested that endothelin serves as an important mediator involved in diseases such as restenosis, prostatauxe, endotoxin shock, endotoxin-induced multiple organ failure or disseminated intravascular coagulation, and cyclosporin-induced renal failure or hypertension.

Two endothelin receptors $ET_A$ and $ET_B$ are known so far and antagonists of these receptors have been shown to be potential drug targets. EP 0526708 A1 and WO 93/08799 A1 are representative examples of patent applications disclosing non-peptidic compounds with alleged activity as endothelin receptor antagonists.

The present invention discloses a process for preparing a compound of Formula I:

Formula I

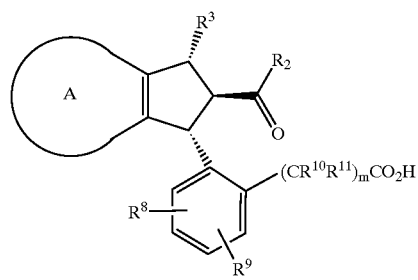

comprising reacting a compound of Formula II,

Formula II

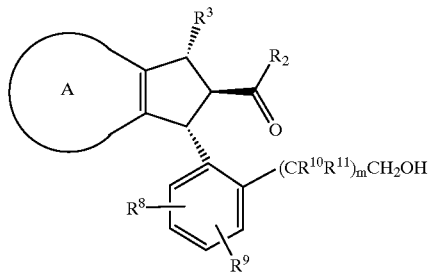

in a solvent with periodic acid and a catalytic amount of a chromium reagent to oxidize to the compound of Formula I.

SUMMARY OF THE INVENTION

The present invention discloses a process for preparing a compound of Formula I:

Formula I

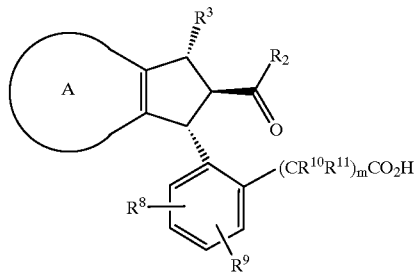

wherein:

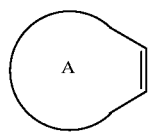

represents:
a) 5- or 6-membered heterocyclyl containing one, two or three double bonds, but at least one double bond and 1, 2 or 3 heteroatoms selected from O, N and S, the heterocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_3$–$C_8$ cycloalkyl, $CO(CH_2)_n CH_3$, and $CO(CH_2)_n CH_2 N(R^5)_2$,
b) 5- or 6-membered carbocyclyl containing one or two double bonds, but at least one double bond, the carbocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_3$–$C_8$ cycloalkyl, $CO(CH_2)_n CH_3$, and $CO(CH_2)_n CH_2 N(R^5)_2$,
c) aryl, wherein aryl is as defined below,
$C_1$–$C_8$ alkoxy, $C_1$–$C_8$ alkyl, or $C_3$–$C_8$ cycloalkyl, are unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_n CH_3$, and $CO(CH_2)_n CH_2 N(R^5)_2$, aryl is defined as phenyl or naphthyl, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, or $C_3$–$C_8$ cycloalkyl, $CO(CH_2)_nCH_3$, $CO(CH_2)_nCH_2N(R^5)_2$, or when aryl is substituted on adjacent carbons they can form a 5- or 6-membered fused ring having one, two or three heteroatoms selected from O, N, and S, this ring is unsubstituted or substituted on carbon or nitrogen with one, two or three substituents selected from the group consisting of: OH, $CO_2R^6$, Br, Cl, F, I, $CF_3$, $N(R^7)_2$, $C_1$–$C_8$ alkoxy, $C_1$–$C_8$ alkyl, $C_3$–$C_8$ cycloalkyl, $CO(CH_2)_nCH_3$, and $CO(CH_2)_nCH_2N(R^5)_2$;

$R^2$ is: $OR^4$ or $N(R^5)_2$;

$R^3$ is:

a) H, b) $C_1$–$C_8$ alkyl, c) $C_1$–$C_8$ alkoxyl, d) $C_3$–$C_7$ cycloalkyl, e) $S(O)_tR^5$, f) Br, Cl, F, I, g) aryl, h) heteroaryl, i) $N(R^5)_2$, j) $NH_2$, k) —CHO, l) —CO—$C_1$–$C_8$ alkyl, m) —CO-aryl, n) —CO-heteroaryl, o) —$CO_2R^4$, or p) protected aldehyde;

heteroaryl is defined as a 5- or 6-membered aromatic ring containing 1, 2 or 3 heteroatoms selected from O, N and S which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_3$–$C_8$ cycloalkyl, $CO(CH_2)_nCH_3$, and $CO(CH_2)_nCH_2N(R^5)_2$, n is: 0 to 5;

t is: 0, 1 or 2;

$R^4$ is: H, or $C_1$–$C_8$ alkyl;

$R^5$ is: H, or $C_1$–$C_8$ alkyl, or aryl;

$R^6$, is: H, $C_1$–$C_8$ alkyl, or aryl;

$R^7$ is: H, $C_1$–$C_8$ alkyl, aryl, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_3$–$C_8$ cycloalkyl, $CO(CH_2)_nCH_3$, $CO(CH_2)_nCH_2N(R^5)_2$; or when two $R^7$ substutients are on the same nitrogen they can join to form a ring of 3 to 6 atom; and $R^8$, $R^9$, $R^{10}$ and $R^{11}$ are independently: H, $C_1$–$C_8$ alkyl, $C_2$–$C_8$ alkenyl, $C_2$–$C_8$ alkynyl, $C_1$–$C_8$ alkoxy, $C_1$–$C_8$ alkylthio, aryl, each of which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_nCH_3$, or $CO(CH_2)_nCH_2N(R^5)_2$;

comprising reacting a compound of Formula II in a solvent,

Formula II

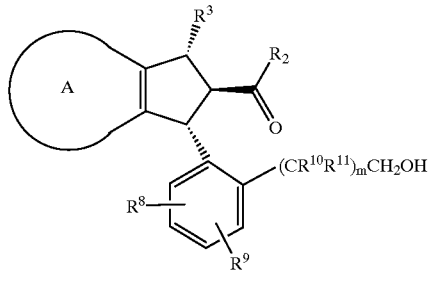

with a solution of periodic acid, a catalytic amount of a chromium reagent in a solvent to oxidize to the compound of Formula I.

DETAILED DESCRIPTION OF THE INVENTION

The present invention discloses a process for preparing a compound of Formula I:

Formula I

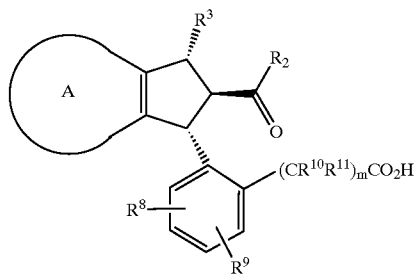

wherein:

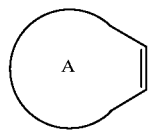

represents:

a) 5- or 6-membered heterocyclyl containing one, two or three double bonds, but at least one double bond and 1, 2 or 3 heteroatoms selected from O, N and S, the heterocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_3$–$C_8$ cycloalkyl, $CO(CH_2)_n CH_3$, and $CO(CH_2)_n CH_2N(R^5)_2$, b) 5- or 6-membered carbocyclyl containing one or two double bonds, but at least one double bond, the carbocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_3$–$C_8$ cycloalkyl, $CO(CH_2)_n CH_3$, and $CO(CH_2)_n CH_2N(R^5)_2$, c) aryl, wherein aryl is as defined below, $C_1$–$C_8$ alkoxy, $C_1$–$C_8$ alkyl, or $C_3$–$C_8$ cycloalkyl, are unsubstituted or substituted with one, two or three substituents selected from the group consisting of: OH, CO$_2$R$^4$, Br, Cl, F, I, CF$_3$, N(R$^5$)$_2$, C$_1$–C$_8$ alkoxy, C$_3$–C$_8$ cycloalkyl, CO(CH$_2$)$_n$CH$_3$, and CO(CH$_2$)$_n$CH$_2$N(R$^5$)$_2$, aryl is defined as phenyl or naphthyl, which is unsubstituted or substituted with one, two or three substituents selected from the group consisting of: OH, CO$_2$R$^4$, Br, Cl, F, I, CF$_3$, N(R$^5$)$_2$, C$_1$–C$_8$ alkoxy, C$_1$–C$_8$ alkyl, or C$_3$–C$_8$ cycloalkyl, CO(CH$_2$)$_n$CH$_3$, CO(CH$_2$)$_n$CH$_2$N(R$^5$)$_2$, or when aryl is substituted on adjacent carbons they can form a 5- or 6-membered fused ring having one, two or three heteroatoms selected from O, N, and S, this ring is unsubstituted or substituted on carbon or nitrogen with one, two or three substituents selected from the group consisting of: OH, CO$_2$R$^6$, Br, Cl, F, I, CF$_3$, N(R$^7$)$_2$, C$_1$–C$_8$ alkoxy, C$_1$–C$_8$ alkyl, C$_3$–C$_8$ cycloalkyl, CO(CH$_2$)$_n$CH$_3$, and CO(CH$_2$)$_n$CH$_2$N(R$^5$)$_2$;

R$^2$ is: OR$^4$ or N(R$^5$)$_2$;

R$^3$ is:

a) H, b) C$_1$–C$_8$ alkyl, c) C$_1$–C$_8$ alkoxyl, d) C$_3$–C$_7$ cycloalkyl, e) S(O)$_t$R$^5$, f) Br, Cl, F, I, g) aryl, h) heteroaryl, i) N(R$^5$)$_2$, j) NH$_2$, k) —CHO, l) —CO-C$_1$–C$_8$ alkyl, m) —CO-aryl, n) —CO-heteroaryl, o) —CO$_2$R$^4$, or p) protected aldehyde;

heteroaryl is defined as a 5- or 6-membered aromatic ring containing 1, 2 or 3 heteroatoms selected from O, N and S, which is unsubstituted or substituted with one, two or three substituents selected from the group consisting of: OH, CO$_2$R$^4$, Br, Cl, F, I, CF$_3$, N(R$^5$)$_2$, C$_1$–C$_8$ alkoxy, C$_1$–C$_8$ alkyl, C$_3$–C$_8$ cycloalkyl, CO(CH$_2$)$_n$CH$_3$, and CO(CH$_2$)$_n$CH$_2$N(R$^5$)$_2$, n is: 0 to 5;

t is: 0, 1 or 2;

R$^4$ is: H, or C$_1$–C$_8$ alkyl;

R$^5$ is: H, or C$_1$–C$_8$ alkyl, or aryl;

R$^6$, is: H, C$_1$–C$_8$ alkyl, or aryl;

R$^7$ is: H, C$_1$–C$_8$ alkyl, aryl, which is unsubstituted or substituted with one, two or three substituents selected from the group consisting of: OH, CO$_2$R$^4$, Br, Cl, F, I, CF$_3$, N(R$^5$)$_2$, C$_1$–C$_8$ alkoxy, C$_1$–C$_8$ alkyl, C$_3$–C$_8$ cycloalkyl, CO(CH$_2$)$_n$CH$_3$, CO(CH$_2$)$_n$CH$_2$N(R$^5$)$_2$; or when two R$^7$ substutients are on the same nitrogen they can join to form a ring of 3 to 6 atom; and R$^8$, R$^9$, R$^{10}$ and R$^{11}$ are independently: H, C$_1$–C$_8$ alkyl, C$_2$–C$_8$ alkenyl, C$_2$–C$_8$ alkynyl, C$_1$–C$_8$ alkoxy, C$_1$–C$_8$ alkylthio, aryl, each of which is unsubstituted or substituted with one, two or three substituents selected from the group consisting of: OH, CO$_2$R$^4$, Br, Cl, F, I, CF$_3$, N(R$^5$)$_2$, C$_1$–C$_8$ alkoxy, C$_1$–C$_8$ alkyl, C$_2$–C$_8$ alkenyl, C$_2$–C$_8$ alkynyl, C$_3$–C$_8$ cycloalkyl, CO(CH$_2$)$_n$CH$_3$, or CO(CH$_2$)$_n$CH$_2$N(R$^5$)$_2$;

comprising reacting a compound of Formula II in a solvent,

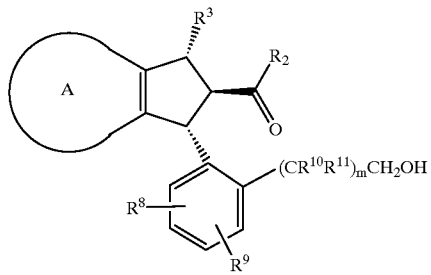

Formula II with a solution of periodic acid, a catalytic amount of a chromium reagent in a solvent at a temperature range of about −20° C. to about 40° C. for about 15 minutes to about 24 hours to oxidize to the compound of Formula I.

The process as recited above, wherein the solvent is selected from the group consisting of: acetonitrile, tetrahydrofuran, diethyl ether, MTBE (methyl t-butyl ether), DME (dimethoxyethane), DIGLYME (2-methoxyethyl ether), TRIGLYME (triethylene glycol dimethyl ether), toluene, benzene, hexane, pentane, dioxane, or a mixture of said solvents, including a mixture of said solvents with water. A small amount of water, about 0.1 to about 10.0 volume percent and preferrably less than 1.0 percent, was found to be beneficial.

The process as recited above wherein the periodic acid (H$_5$IO$_6$) is utilized in about 2.0 to about 4.0 equivalents, preferably about 3.5 equivalents. A minimum of two equivalents of periodic acid are needed to carry out the oxidation from a primary alcohol to a carboxylic acid. Additionally, if the compound of Formula II contains any basic functional groups, an additional equivalent of periodic acid for each basic functional group will be needed to carry out the oxidation.

The process as recited above, wherein the chromium reagent is selected from the group consisting of: CrO$_3$, Na$_2$Cr$_2$O$_7$, K$_2$Cr$_2$O$_7$, CrX$_3$, where X is Cl, Br, F, NO$_2$, OAc, or ClO$_4$. The process as recited above, wherein the chromium reagent is utilized in about 0.1 to about 10 mole percent, preferably about 1.0 to about 2.0 mole percent.

The process as recited above, wherein the temperature range is about −20° C. to about 30° C., and preferably about −10° C. to about 0° C. The process as recited above, wherein the reaction time is about 15 minutes to about 24 hours and preferably between about 45 minutes and about 1.5 hours.

The process as recited above, wherein the compound of Formula I is

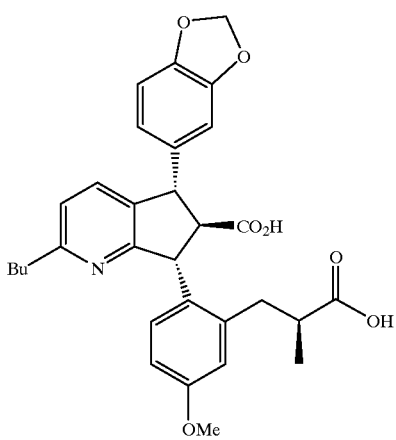

and the compound of Formula II is

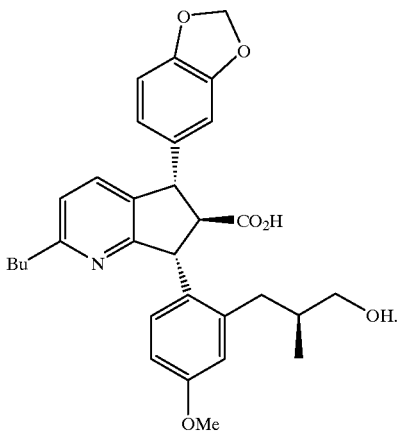

A process for the preparation of a compound of Formula I

Formula I

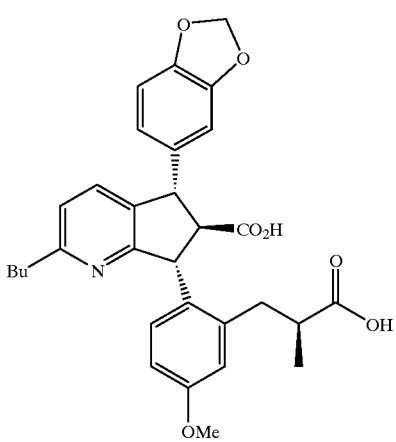

comprising reacting a compound of Formula II in a solvent,

Formula II

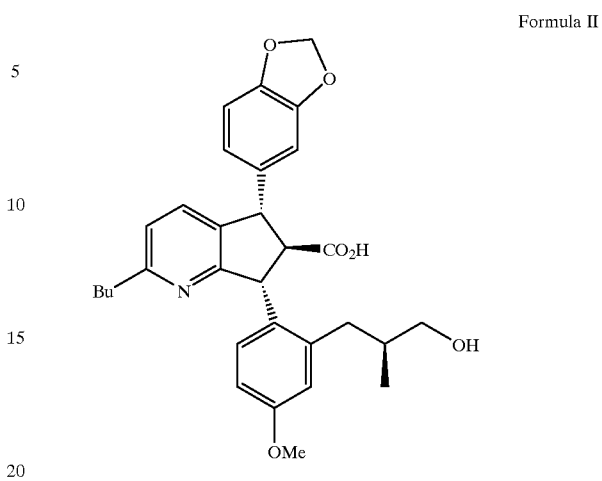

with a solution of periodic acid, a catalytic amount of chromium trioxidize in a solvent at a temperature range of about −20° C. to about 30° C. for about 15 minutes to about 24 hours to oxidize to the compound of Formula I.

It is further understood that the substituents recited above would include the definitions recited below.

The protected aldehyde substitutent recited above denotes those aldehyde protecting groups outlined by Greene and Wuts in Chapter 4 of "Protective Groups in Organic Synthesis" 2nd Edition, John Wiley & Son, Inc. (1991).

The alkyl substituents recited above denote straight and branched chain hydrocarbons of the length specified such as methyl, ethyl, isopropyl, isobutyl, tert-butyl, neopentyl, isopentyl, etc.

Cycloalkyl denotes rings composed of 3 to 8 methylene groups, each of which may be substituted or unsubstituted with other hydrocarbon substituents, and include for example cyclopropyl, cyclobutyl, cyclopentyl, cyclohexyl and 4-methylcyclohexyl.

The alkoxy substituent represents an alkyl group as described above attached through an oxygen bridge.

The aryl substituent represents phenyl and 1-naphthyl or 2-naphthyl, including aryls substituted with a 5- or 6-membered fused ring, such as an unsubstituted and substituted methylenedioxy, oxazolyl, imidazolyl, or thiazolyl ring.

The heteroaryl substituent represents a carbazolyl, furanyl, thienyl, pyrrolyl, isothiazolyl, imidazolyl, isoxazolyl, thiazolyl, oxazolyl, pyrazolyl, pyrazinyl, pyridyl, pyrimidyl, purinyl.

The heterocyclyl substituent represents a pyridyl, pyrimidyl, thienyl, furanyl, oxazolidinyl, oxazolyl, thiazolyl, isothiazolyl, pyrazolyl, triazolyl, imidazolyl, imidazoldinyl, thiazolidilnyl, isoxazolyl, oxadiazolyl, thiadiazolyl, morpholinyl, piperidinyl, piperazinyl, pyrrolyl, or pyrrolidinyl.

The α,β-unsaturated ester or amide

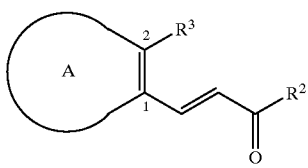

can generally be prepared in two steps:

1) a coupling reaction at the one position of Ring A

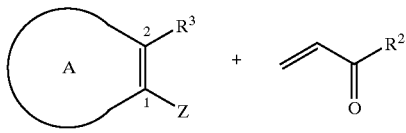

wherein $R^3$ is CHO, Z is a leaving group, such as Br, Cl, I, OTriflyl, OTosyl or OMesyl and $R^2$ is $OR^4$ or $N(R^5)_2$; and 2) the conversion of the aldehyde ($R^3$=CHO) to the desired

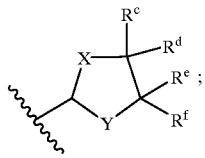

chiral auxiliary ($R^3$), wherein $R^3$ represents X and Y are independently: O, S, or $NR^5$; $R^4$ is $C_1$–$C_8$ alkyl; $R^5$ is: $C_1$–$C_8$ alkyl, or aryl; $R^c$, $R^d$, $R^e$ and $R^f$ are independently: H, $C_1$–$C_8$ alkyl, and aryl, such that either $R^c$ and $R^d$ are not the same and/or $R^e$ and $R^f$ are not the same, or $R^c$ and $R^e$ or $R^d$ and $R^f$ can join to form a 5- or 6-membered ring, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, or $C_3$–$C_8$ cycloalkyl, $CO(CH_2)_nCH_3$, $CO(CH_2)_nCH_2N(R^5)_2$; and n is 0 to 5.

Commercially available pyridone 1 is alkylated via its dianion with propyl bromide, and the product is then converted into the bromopyridine 3a using a brominating agent such as $PBr_3$. The nitrile 3a is then reduced to the aldehyde 3 using diisobutyl aluminum hydride (DIBAL). The aldehyde then undergoes a Heck reaction with t-butyl acrylate using NaOAc, $(allyl)_2PdCl_2$, tri-o-tolylphosphine, toluene, reflux to provide the unsaturated ester 4a in high yield. The unsaturated ester 4a is then heated with pseudoephedrine, or alternatively, N-methyl-cis-aminoindanol (not shown in the schemes), and acetic acid in toluene to give the protected aldehyde 5.

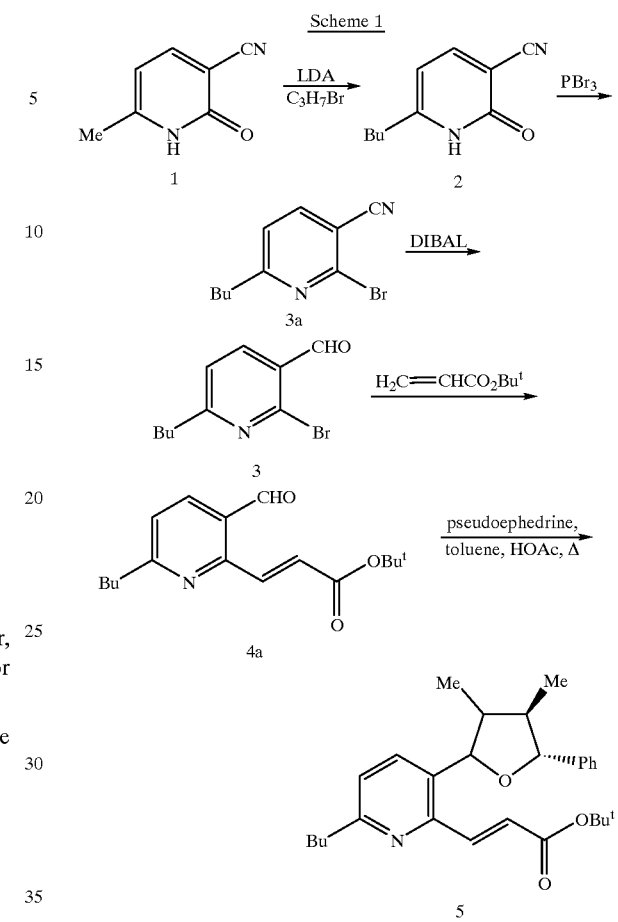

Commericially available acid 10 is reduced with in situ borane ($NaBH_4/BF_3.Et_2O$) to the alcohol 11, which is then converted into the chloride 13, by treatment with $SOCl_2$ in dimethylformamide (DMF).

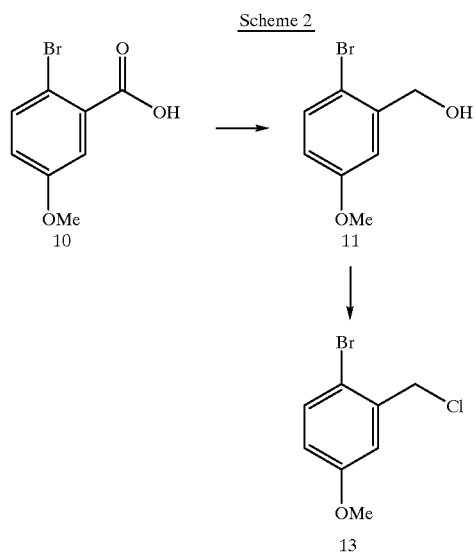

Commercial available 1,2-aminoindanol 7 is acylated (propionyl choride, $K_2CO_3$) to give amide 8, which is then converted into the acetonide 9 (2-methoxypropene, pyridinium p-toluene-sulfonate (PPTS)). Acetonide 9 is then alkylated with the benzylchloride 13, (LiHMDS) to give 14, which is then hydrolyzed (6N HCl, dioxane) to give the carboxylic acid 15. Reduction (NaBH$_4$/BF$_3$.Et$_2$O) of the acid provided the alcohol 16 in high yield and optical purity. Protection of the alcohol 16 (TBSCl, imidazole) provided bromide 17, the precursor to organolithium 17a.

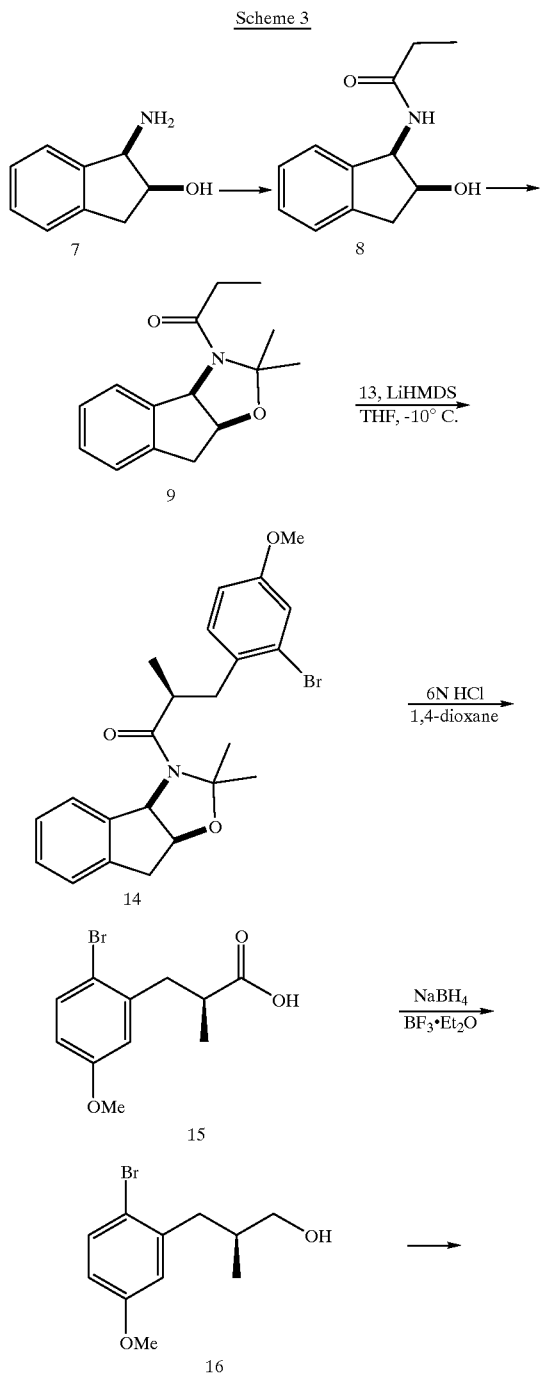

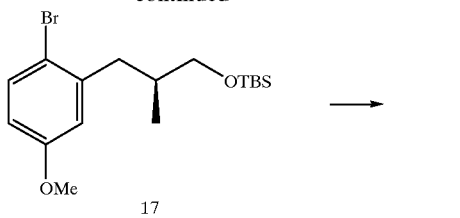

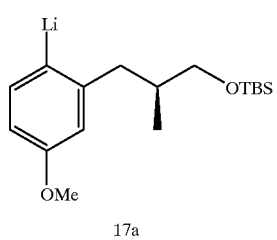

Compound 17a is added to the α,β-unsaturated ester bearing a pseudoephedrine 5 (or the N-methyl-cis-aminoindanol chiral auxiliary, not shown) at −78° to −50° C. Work up with acid, THF and water (to remove the auxiliary) affords compound 6 in high yield and good stereoselectivity. Please note other chiral axillary groups can be utilized in this asymmetric addition. See WO 98/06698, published by the World Intellectual Property Organization on Feb. 19, 1998.

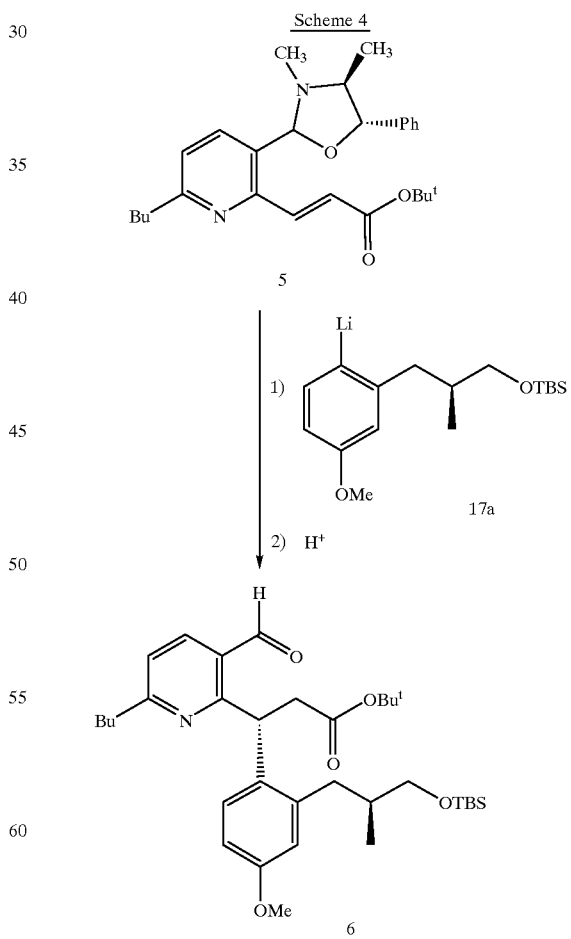

Addition of the Grignard reagent (prepared from the aryl bromide and magnesium) to compound 6 at −78° C. to about −60° C. in THF affords compound 7 in quantitative yield and good stereoselectivity.

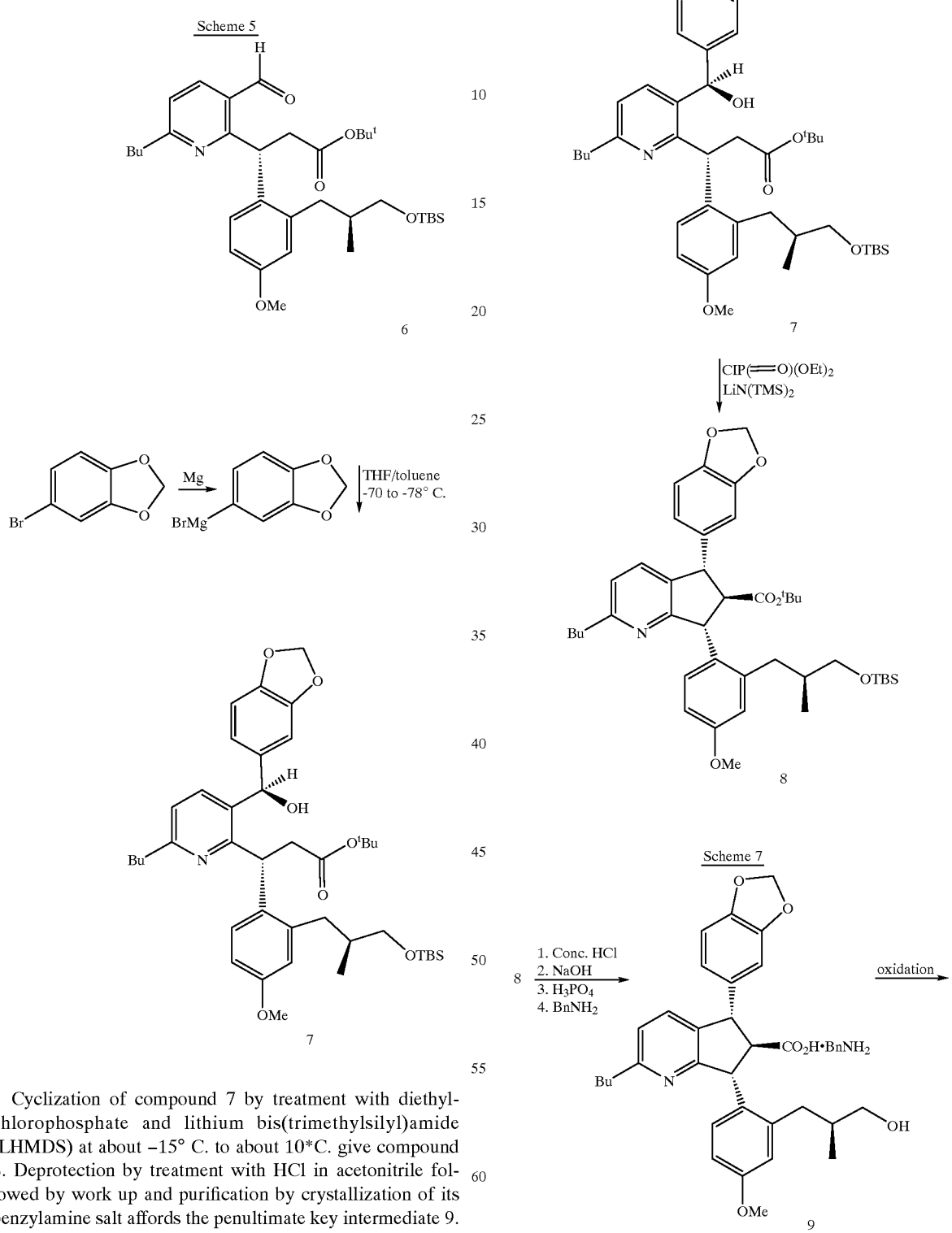

Cyclization of compound 7 by treatment with diethylchlorophosphate and lithium bis(trimethylsilyl)amide (LHMDS) at about −15° C. to about 10*C. give compound 8. Deprotection by treatment with HCl in acetonitrile followed by work up and purification by crystallization of its benzylamine salt affords the penultimate key intermediate 9.

-continued

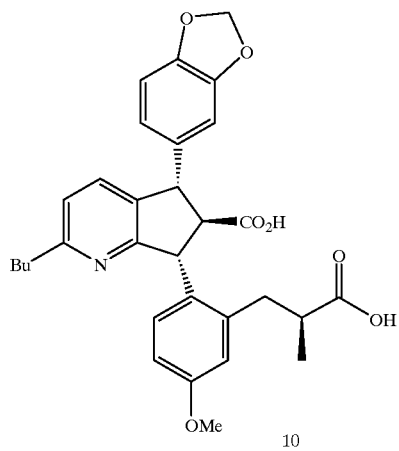

Salt breaking followed by oxidation of the primary lacohol 9 according to the present invention gives the dicarboxylic acid 10 in high yield.

Scheme 8

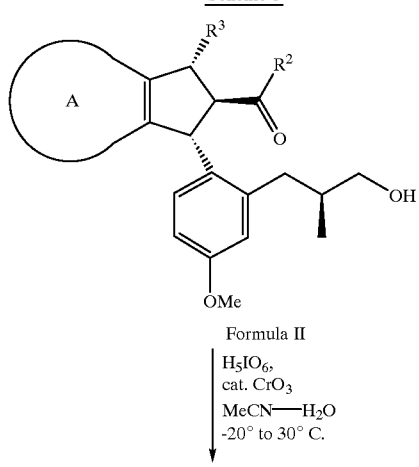

Formula II

H₅IO₆,
cat. CrO₃
MeCN—H₂O
-20° to 30° C.

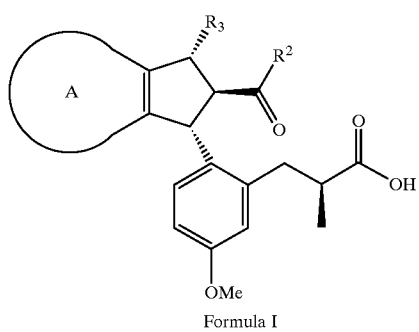

Formula I

The instant invention can be understood further by the following examples, which do not constitute a limitation of the invention.

EXAMPLE 1

Preparation of 2-bromo-5-methoxybenzyl alcohol

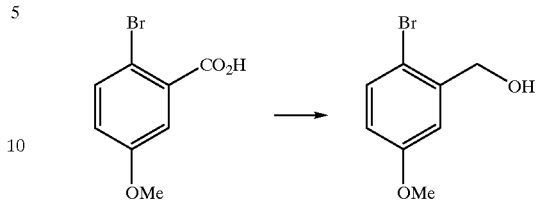

Sodium borohydride (8.6 g) is slurried in THF (150 mL KF=150 μg/mL) in a round bottom flask equipped with a thermocouple, an addition funnel, a nitrogen inlet a mechanical stirrer and a cooling bath. 2-Bromo-5-methoxybenzoic acid (50 g) is dissolved in THF (100 mL KF=150 μg/mL) is added to the sodium borohydride slurry over 45 min while maintaining the temperature at 20–25° C. The reaction must be controlled with intermittent cooling and by careful monitoring of the addition rate. The mixture is aged for 30 min at 20–25° C. Boron trifluoride etherate (36.9 g) is added over a period of 30 min at 30–35° C.

The addition of boron trifluoride etherate produces a delayed exotherm and should be added slowly in order to control the reaction temperature. The resulting white slurry is aged for 1 h at 30–35° C. and then sampled for HPLC assay. A peak at RT=8.7 min is an impurity related to the starting material. The acid is at RT=9.1 min.

The reaction mixture is cooled to 15° C. and carefully quenched into a cold (10° C.) saturated ammonium chloride solution (150 mL) while maintaining the temperature<25° C.

Ethyl acetate (500 mL) is added and the layers are separated. The organic layer is washed with water (100 mL) and then transferred to a 1 L round bottom flask equipped for distillation. The solution was concentrated and charged with fresh ethyl acetate. This is repeated until a solution with a volume of 200 mL has KF<200 μg/mL. The solvent is then switched to DMF to give the final volume of 200 mL with a KF<200 μg/mL.

EXAMPLE 2

Preparation of 2-bromo-5-methoxybenzyl chloride

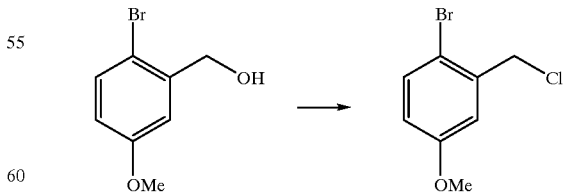

The DMF solution of the benzyl alcohol (91.3 g in 400 mL KF=300 μg/mL) is charged to a 2 L flask equipped with a mechanical stirrer, thermocouplee, N₂ inlet, and cooling bath. The solution is cooled to 0–5° C. and the addition funnel is charged with thionyl chloride (55.0 g). The thionyl chloride is added over a period of 45 min while maintaining the temperture 5–10° C. The mixture is aged for 1 h at 5° C. and assayed by HPLC.

The addition funnel is charged with water (400 mL) which is added dropwise to the reaction mixture over a period of 30 min. while maintaining the temperture<15° C. The temperature is controlled by cooling and monitoring the rate of addition. The initial addition of water is highly exothermic. Using large excess of thionyl chloride results in a more exothermic quench. If the quench temperature is not controlled, hydrolysis of the benzyl chloride back to the alcohol may result.

The resulting thick white slurry is aged for 1 h at 0–5° C. The benzyl chloride is isolated by filtration. The cake is washed with (1:1) DMF:H$_2$O (100 mL) and then water (200 mL). The solid is dried in vacuo to give 93 g of the benzyl chloride (94% yield, 96 A %). HPLC assay: Column: Waters Symmetry C8, 4.6×250 mm; UV Detection: 220 nm; Column Temp: 25° C.; Flow rate: 1 mL/min.; Eluent: CH$_3$CN:H$_2$O:0:0.1% H$_3$PO$_4$ (70:30); RT (benzyl alcohol)= 3.9 min; RT (benzyl chloride)=7.3 min.; and RT (DMF)=2.6 min.

EXAMPLE 3

Preparation of the Acetonide of N-propanoyl (1R, 2S)-cis-aminoindanol

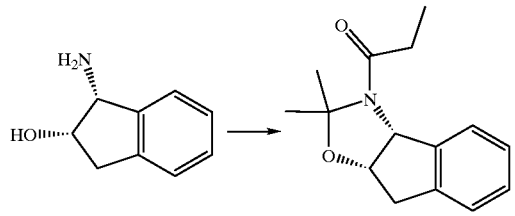

A 5 L 3-neck round bottom flask equipped with a mechanical stirrer, N$_2$ inlet, thermocouple probe, heating mantle, and addition funnel is charged with (1R,2S)-cis-aminoindanol (100 g), tetrahydrofuran (1.2 L, KF 120 μg/mL), and triethylamine (96 mL, KF 500 μg/mL). The resulting slurry is heated under a N$_2$ atmosphere to 40–45° C. giving a yellow solution. Propionyl chloride (59 mL) is charged to an addition funnel and added to the solution while maintaining the temperature at 45–50° C.

The temperature is controlled by rate of propionyl chloride addition and a cooling bath. HPLC assay shows >99% amide formed. Methanesulfonic acid (3 mL) is added to the reaction slurry. 2-Methoxypropene (140 mL) is charged to an addition funnel and added over 30 minutes at a temperature of 50° C.

The addition of 2-methoxypropene is mildly exothermic. The temperature is maintained by the rate of addition and a heating mantle. The reaction remains a slurry but does become less thick.

The reaction slurry is aged for 1–2 hours at 50° C. HPLC assay at this point shows <0.5 A % of the amide remaining. The amide is not removed in the isolation so it is important to push the reaction to completion. The reaction slurry is cooled to 0–5° C. and quenched by addition of 5% aqueous sodium carbonate solution (1 L) and heptane (1 L). The layers are stirred and separated and the organic is washed with water (300 mL).

HPLC assay at this point shows the acetonide in >98 A % and >90% yield. The acetonide/THF/heptane solution is filtered into a 2 L round bottom flask and the solution is distilled to a final volume of 700 mL. Heptane (1 L) is added and the solution is distilled to a final volume of 700 mL. The distillation is done under partial vacuum at ~50° C. NMR assay at this point shows<2 mol % THF. The solution is allowed to cool and is seeded with acetonide at 35–40° C. The thick slurry is aged for 1 hour at ambient temperature then cooled to 0–5° C. and aged for 1 hour. The slurry is filtered and the cake is washed with cold heptane (200 mL) and air dried to yield acetonide as a crystalline white solid (141.1 g, 85% yield, 99.6 A %).

EXAMPLE 4

Alkylation of the Acetonide with 2-bromo-5-methoxybenzyl chloride

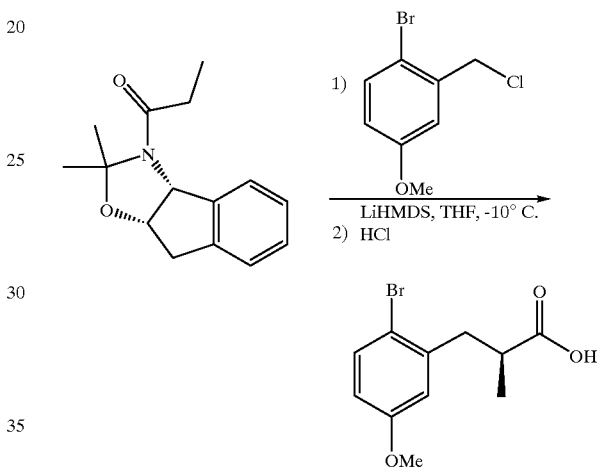

A THF solution (2L, KF<200 μg/mL) of the acetonide (252 g) and the benzyl chloride (255 g) is cooled to −10° C. Lithium bis(trimethylsilyl)amide (1.45 L) is added dropwise over 5 h at 0–2° C. The mixture is then aged for 1.5 h and assayed by HPLC.

The reaction is quenched by adding aqueous saturated ammonium chloride solution (1 L). The initial addition of the ammonium chloride should be slow in order to control the foaming. The rate can be increased when the foaming subsides.

The quenched reaction is then transfered into a mixture of aqueous ammonium chloride (1.5 L), water (0.5 L), and ethyl acetate (3 L). The mixture is then agitated for 15 min and the layers are separated. The organic layer is washed with water (1 L) and brine (0.5 L). The ethyl acetate solution is concentrated to a low volume and solvent switched to 1,4-dioxane. The dioxane solution is adjusted to a final volume of 1.8 L.

The dioxane solution of the coupled product is charged to a 12 L round bottom flask and 6 M HCl (1.5 L) is charged. The mixture is heated to reflux and monitored by HPLC.

The mixture is cooled to 20° C. and MTBE (3 L) is added. The mixture is agitated for 15 min and the layers are separated. The organic layer is washed with water (1 L). The MTBE solution of the crude acid is extracted with 0.6 M sodium hydroxidize (2 L). The aqueous solution of the sodium salt of the acid is combined with MTBE (2.5 L) and cooled to 10° C.

The two phase mixture is acidified with 5.4 M sulfuric acid (250 mL), agitated for 15 min, settled and the layers separated. The MTBE solution of the acid is washed with water (0.5 L). The MTBE solution of the acid is dried by distilation and then solvent switched to THF. The final volume of the THF is 2 L with a KF<250 μg/mL.

HPLC assay: column: Waters Symmetry; Eluent: acetontrile: water:phosphoric acid (70:30:0.1); Flow rate: 1 mL/min.; RT (acetonide)=4.5 min.; RT (benzyl chloride)= 7.5 min.; RT (coupled product)=11.5 min.; RT (aminondanol)=1.7 min.; RT (hydroxyamide)=1.7 min.; and RT (acid)=4.5 min.

EXAMPLE 5

Preparation of 3-(2-bromo-5-methoxyphenyl)-2-methylpropanol

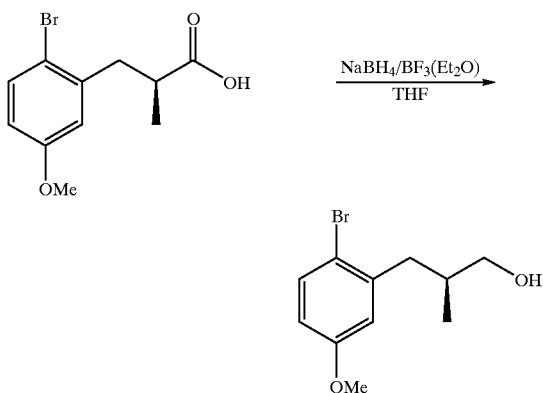

Sodium borohydride (33 g) is slurried in THF (0.5 L KF=200 μg/mL) in a round bottom flask. The THF solution (2 L) of the acid is added to the sodium borohydride slurry over 1 h while maintaining the temperature at 20–25° C.

The reaction is controlled with a cooling bath and by carefully monitoring the addition rate. A nitrogen sweep and proper venting of the hydrogen is also important.

The mixture is aged for 30 min at 20–25° C. Boron trifluoride etherate (152 g) is added over 1 h at 30–35° C. The addition produces a delayed exotherm and should be carefully monitored in order to control the reaction temperature. The resulting milky white slurry is aged for 1 h at 30° C. and sampled for HPLC assay.

The reaction mixture is cooled to 15° C. and carefully quenched in a cold (10° C.) ammonium chloride solution (1.5 L) while maintaining the temperature at 25° C. The rate of hydrogen evolution is controlled by the rate of the addition of the mixture into the ammonium chloride. The quenched mixture is distilled in vacuo to remove the THF. The aqueous layer is extracted with MTBE (1.5 L) and the organic layer is dried by flushing with additional MTBE. The MTBE solution is then solvent switched to hexanes and adjusted to a volume of 350 mL and seeded. The slurry is aged for 2 h at 20° C. and then cooled to 0–5° C. aged for 1 h and filtered. The cake is washed with cold hexanes (200 mL). The solid is dried under a nitrogen sweep. The isolated solid (164 g) is >99 A % by HPLC and >99% ee.

HPLC: Column: Waters Symmetry C8; Solvent: acetonitrile:water: phosphoric acid (50:50:0.1); Flow rate: 1 mL /min.; Detection: 220 nm; RT (acid)=10.2 min.; RT (alcohol)=10.7 min.

Chiral HPLC: Column: Chiracel OD-H; Hexane:2-propanol (97:3); Flow rate: 1 mL/ min.; Detection: 220 nm; RT minor isomer=21 min.; and RT major isomer=23 min.

EXAMPLE 6

Preparation of 3-(2-bromo-5-methoxyphenyl)-2-methylpropyl t-butyldimethylsilyl ether

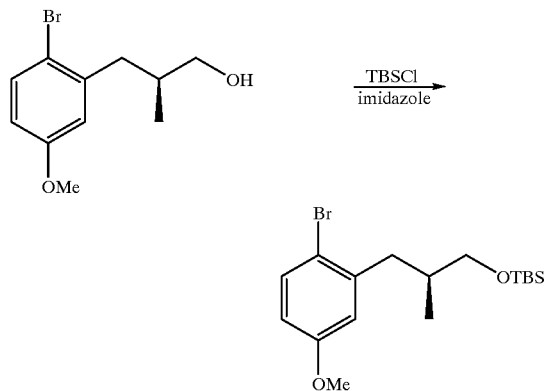

Imidazole (1.6 g, 0.023 mol) is added to a solution of the alcohol (5.0 g, 0.019 mol) in DMF (15 mL) at 20° C. The addition of imidazole is endothermic and results in a 4–5° C. drop in temperature. TBSCl (3.0 g, 0.020 mol) is dissolved in DMF (5 mL) and is added slowly to the above solution while maintaining the temperature 20–25° C. using a cooling bath. The reaction is monitored by HPLC.

MTBE (50 mL) is added to the reaction mixture along with water (50 mL) and the phases are separated. The organic is washed with water (50 mL) and then concentrated to 10 mL total volume and solvent switched into THF in preparation for the next step. NMR assay of the organic layer after the second water wash indicates no residual DMF. This is crucial because DMF may be problematic in the next step.

$^1$H NMR (CDCl$_3$) δ: 7.41 (d, J=8.74, 1H), 6.77 (d, J=3.04, 1H), 6.63 (dd, J=8.73, 3.06, 1H), 3.78 (s, 3H), 3.50 (d, J=5.75, 2H), 2.89 (dd, J=13.31, 6.15, 1H), 2.45 (dd, J=13.30, 8.26, 1H), 2.03 (m, 1H), 0.94 (s, 9H), 0.92 (d, J=5.01, 3H), 0.07 (s, 6H).

$^{13}$C NMR (CDCl$_3$) δ: 159.1, 141.6, 133.2, 117.0, 115.4, 113.2, 67.4, 55.4, 39.7, 36.3, 26.0 (3C), 18.4, 16.5, −5.3 (2C).

HPLC assay: column, Zorbax Rx C8 (4.6×250 mm); solvent:acetonitrile:water:phosphoric acid 90:10:0.1; flow rate: 1 mL /min; UV Detection: 220 nm; Retention times: RT (alcohol)=3.08 min; RT (DMF)=3.17 min; and RT (product)=7.7 min.

EXAMPLE 7

Pseudoephedrine Acetal Formation of t-butyl 3-(6-n-butyl-3-formylpyridyl)-2-prop-2-enoate

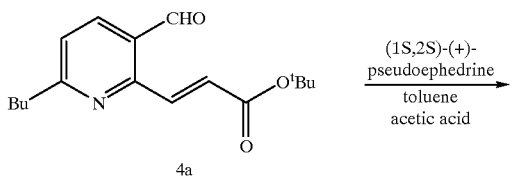

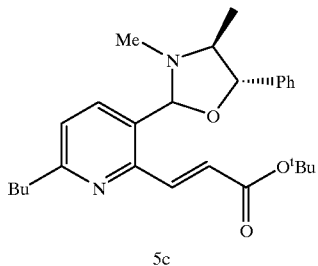

5c

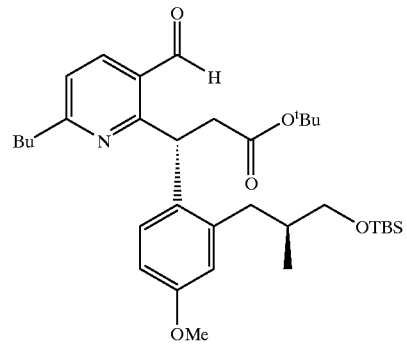

To a solution of Heck product 4a (2.907 kg) in toluene (7.049 kg) is added solid (1S,2S)-(+)-pseudoephedrine (1.74 kg) followed by acetic acid (2.87 ml). The reaction mixture is then heated to reflux. The toluene/water azeotrope begins to reflux at a pot temperature of 87° C. Over the course of 40 minutes, the pot temperature increases to 110° C. At this time, approximately 160 ml of water has been collected in the Dean-Stark trap.

A HPLC assay of an aliquot indicates that all starting Heck product has been consumed.

The reaction is then cooled to 40° C. and pumped into a 50 L extractor and diluted with MTBE (10.67 kg). The organic layer is washed with saturated NaHCO$_3$ (12.10 kg) and then with water (23.64 kg). The organic layer is concentrated to a volume<10 L and a KF<120 µg/mL. The MTBE is removed prior to flushing with toluene. Typically 8–10 L of toluene is required as flush to obtain the desired KF. The dry toluene solution was stored under nitrogen until needed.

HPLC Assay: Column: Zorbax Rx-C8 4.6×250 mm; Solvent:Acetonitrile:water 95:5; Flow: 1.0 mL /min; UV Detection: 220 nm; RT (toluene)=3.2 min.; RT (Heck Product)=3.9 min.; and RT (N,O, acetal)=5.3 min.

EXAMPLE 8

Conjugate Addition-Hydrolysis

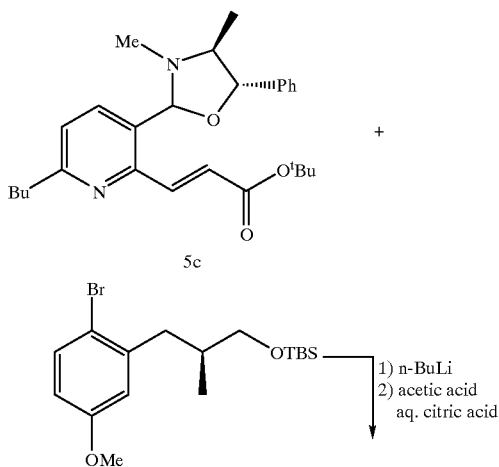

1) n-BuLi
2) acetic acid
   aq. citric acid

To a solution of arylbromide (4.08 kg) in THF (7.34 kg, KF<150 µg/mL) at −82° C. is added a 2.25 M solution of n-BuLi in hexanes (4.87 L). The addition takes 2 h and the internal temperature is maintained below −72° C.

Assay by HPLC indicates that the lithiation is complete after addition of the n-BuLi. The lithiation reaction is instantaneous at the reaction temperature. The purpose of checking an aliquot is to insure that the proper amount of n-BuLi is charged. To the above solution (re-cooled to approximately −80° C.) is added the pre-cooled (approximately −65° C.) toluene solution (KF<150 µg/mL) of the enoate. The addition is done very rapidly with the aid of a pump (addition time<5 min.) and the reaction typically exotherms to −32° C.

In order to insure efficient pumping, the enoate solution was diluted with an additional 3–4 L of toluene.

The reaction is re-cooled to −60° C. and quenched carefully with 2.9 L of acetic acid. (Warning: exothermic reaction.) The reaction exotherms to approximately −20° C. The quenched reaction mixture is then pumped into a 100 L extractor. A citric acid solution (4.82 kg of citric acid in 8 kg of water) is then added and the two-phase mixture is rapidly stirred for 16 h at room temperature. HPLC assay indicates that the N, O acetal hydrolysis is complete.

The phases are cut and the aqueous layer is extracted with MTBE (14.23kg). The combined organic layers are washed twice with 5% NaHCO$_3$ (2×23 kg). The organic layer is then washed with water (20.55 kg). The pH of the water wash should be neutral to slightly basic. The organic layer is dried under reduced pressure to a volume<7 L and a KF<100 µg/mL. The MTBE is removed prior to flushing with toluene. Approximately 30 kg of toluene is needed as flush to obtain the desired KF value. The dry toluene solution is then pumped into a plastic carboy. The 100 L extractor and pump are then flushed with 2.5 kg of THF. HPLC assay indicates a yield of 4.2 kg (72% from the Heck Product, 3 steps). The ee of the product is determined to be 92%.

HPLC Assay: Column: Zorbax Rx-C8 4.6×250 mm; Solvent:acetonitrile:water 95:5; flow rate: 1.0 mL /min.; UV Detection: 220 nm; RT (toluene)=3.2 min.; RT (ArH)=5.5 min.; RT (ArBr)=6.5 min.; RT (ArBu)=8.2 min.; RT (Aldehyde Product)=9.5 min.; and RT (N,O acetal Product)= 18.2 min.

Chiral HPLC Assay: Column: Whelk-O; Solvent: 97:3 Hexane/IPA; flow rate=1.0 mL/min.; RT(toluene)=3.1 min.; RT(minor)=6.8 min.; and RT(major)=7.5 min.

EXAMPLE 9

Grignard Addition

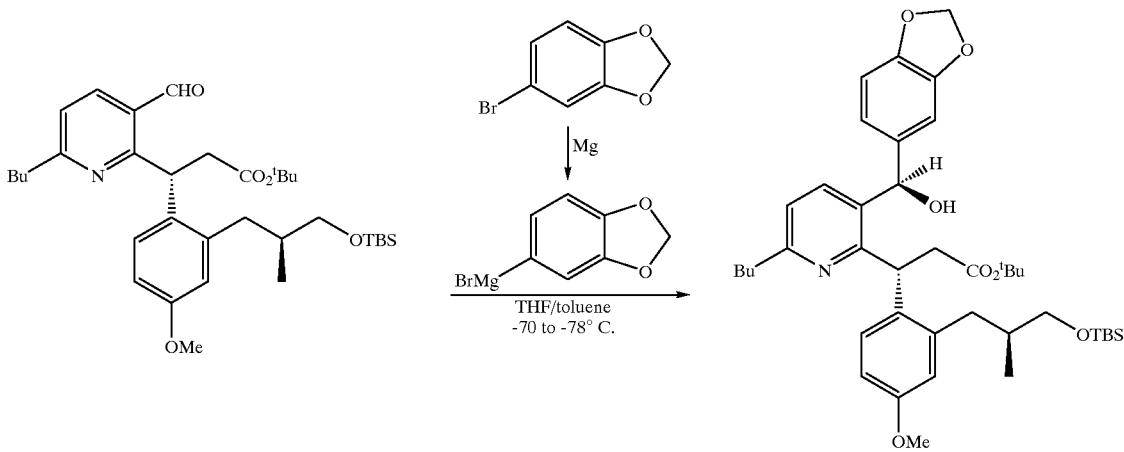

Step A: Preparation of the Grignard Reagent

To a 22 L reaction flask equipped with an efficient condenser is charged Mg (240 g, 9.87 mol) and dry THF (8.2 L, KF<100 μg/mL). The mixture is heated to 50° C. after degassing by two vacuum/$N_2$ cycles. The aryl bromide (1.89 kg, 9.40 mol) is then added carefully!

Due to the induction period and very exothermic reaction, the ArBr should be added very carefully! No more than 10% of the ArBr should be added before the reaction is initiated as indicated by the exotherm (the batch temperature will be higher than that of the bath) and color change from colorless to pale yellow. Cooling maybe required to control the reaction temperature. Once the reaction is initiated, the heating is stopped and the remaining ArBr is added slowly maintaining a gentle reflux. The reaction mixture is then aged at 50° C. for 2 hours to give a solution of ArMgBr (~9.4 L, 1.0 M). The reaction is monitored by HPLC. Zorbax SB-C8 4.6×250 mm, 30° C.; 1.50 mL/min; linear gradient: MeCN 40–70% in 15 min, 0.1% $H_3PO_4$; 220 nm; Retention time (min.): ArBr, 6.2; ArH, 9.2 min.

Step B: Addition of the Grignard Reagent to the Aldehyde

A dry solution of the crude Michael addition product (4.22 kg in ~4.7 L toluene and 2.5 L THF, KF<200 μg/mL) is charged into a 72 L flask. Dry THF (20 L, KF<100 μg/mL) is added and the mixture is degassed by a vacuum/$N_2$ cycle. After the batch is cooled to –75° C. with a dry ice-methanol bath, the ArMgBr prepared above is added slowly maintaining the batch below –65° C. The mixture is aged at –70° C. for 1 hour and the completion of the reaction is confirmed by HPLC (<1 A % aldehyde). The reaction mixture is aged for two more hours then pumped into aqueous $NH_4Cl$ (14 L 20 w %) to quench the reaction. Toluene (14 L) is added and the mixture is warmed to 20° C. The organic layer is separated and washed with brine (14 L) to give a solution of the crude Grignard addition product (50.11 Kg).

Assay by HPLC indicates the presence of 4.67 Kg (91% yield) of the product in solution. It is dried with ~2 kg of anhydrous $Na_2SO_4$ overnight to remove the bulk of the water then filtered and concentrated to 15 L under vacuum. The KF of the residue should be below 150 μg/mL (flush with additional toluene as needed). It is used directly for the cyclization.

HPLC conditions: Column: Zorbax SB-C8 4.6×250 mm; temperature: 30° C.; Solvent: $CH_3CN:H_2O:0.1H_3PO_4$ 80:20:0.1 gradient to 100:0:0.1 over 15 min.; Flowrate: 1.5 mL/min.; RT (aldehyde)=12.15 min.; RT (major stereoisomer)=9.93 min.; RT (minor stereoisomer)=10.65 min.

EXAMPLE 10

Cyclization-Deprotection

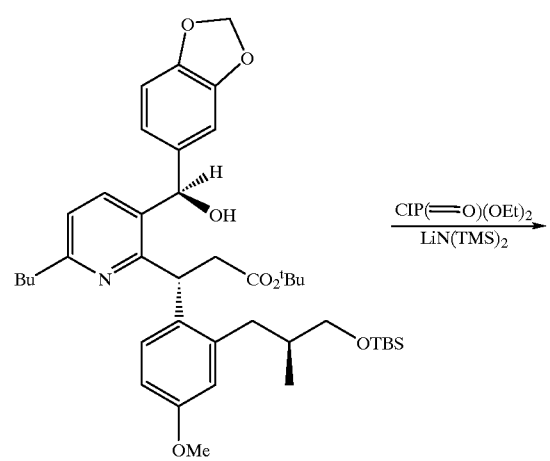

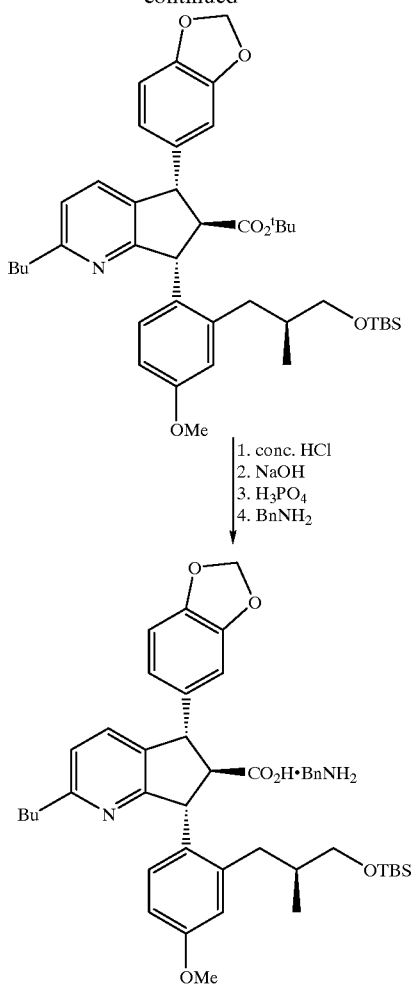

The Grignard addition product in toluene (~15 L, KF=130 μg/ml) is cooled to −15° C. and the diethylchorophosphate (1.65 kg, 9.6 mol, 1.45 eq) is added. Then LiN(TMS)$_2$ in THF (1.0 M, 28.75 L, 4.35 eq) is added while keeping the temparature<5° C. The slurry is aged at 0–10° C. for 4 hrs. More diethyl chlorophosphate and LiN(TMS)$_2$ may be added as required to complete the reaction. The reaction is monitored by HPLC. After 3 h the reaction is typically complete. After the reaction is completed (SM<1%), water (17 L) and acetic acid (4.5 kg, exothermic!) is added while keeping the reaction temperature<30° C.

The temperature is controlled by controlling the rate of addition and by using a cooling bath. After the two layers are separated, the organic layer is washed with 14 L brine. The organic layer is concentrated under vacuum to minimum volume of 10–12 L and mixed with 20 L acetonitrile and then cooled to 0° C. Concentrated HCl (13.2 kg) is added slowly while keeping the reaction temperature <25° C. The mixture is aged at 20–25° C. overnight.

The product is a mixture of the acid alcohol and the lactone. HPLC (same column and eluents) Time 0 A/B 50/50, 10 min A/B 90/10, 15 min 90/10. Retention time t-butyl ester alcohol 6.4 min, lactone 4.7 min, acid alcohol 2.9 min.

When the t-butyl ester alcohol is consumed (19 hrs), the reaction mixture is cooled to 0° C. and 40% w/w NaOH (~12.4 kg until pH=3–5) is added while keeping the temperature <25° C. Water (6 L) is also added. When the pH of the aqueous layer reaches 3, the two layers are separated. The top organic layer is then mixed with 3.3 kg 40% NaOH (5 eq) and 12 L water. The mixture is vigorously stirred for 3 hrs until all the lactone is consumed (organic layer sample). The two layers are then separated and to the organic layer is added 20 L MTBE and 20 L water and 200 g 40% NaOH. The two layers are separated again after mixing. The organic layer is mixed with 100 g 40% NaOH, 10 L water and 20 L heptane. The layers are separated and the organic layer discarded.

To the combined aqueous layer is added H$_3$PO$_4$ (85%, 4.6 kg, 6 eq) until pH=3–4 (exothermic, keep the temperature<25° C.) and MTBE (12 L). After the two layers are separated, the aqueous layer is extracted with 20 L toluene. The combined organic layer is dried with 1.5 kg Na$_2$SO$_4$ and then concentrated under vacuum to a volume of ~10 L. It was flushed with 5 L toluene to reach KF=450 μg/ml. The residue is then mixed with 50 L MTBE. Benzylamine (0.85 kg, 1.2 eq) is added as a solution in 3 L MTBE. Only 1.5 L of this solution is added initially and the batch is seeded with 0.5 g L-321,865 benzylamine salt. The batch is aged for one hour for the salt to precipitate. The rest of the benzylamine solution is added over 30 min. Additional 7 L MTBE is used for rinse. The batch is aged at ambient temperature overnight. The solid is collected by filtration and washed with 3×4 L MTBE until the wash is nearly colorless. The batch is dried with nitrogen flow and suction, wt. 2.96 kg (72% yield). HPLC showed ~95 wt % pure and 98.5 area %.

HPLC: Column: Zorbax SB C-8 column 4.6×250 mm size; Solvent: Eluent: A: MeCN and B: 0.1% H$_3$PO$_4$; Gradient: Time 0 A/B 80/20, 10 min 95/5; 20 min A/B 98/2; 25 min 98/2; Flow rate: 1.5 ml/min; UV detection: 220 nm; RT (Grignard product)=10.9 min.; RT (intermediate)=11.7 min.; RT (intermediate)=13.2 min.; RT (product)=12.2 min

EXAMPLE 11

Oxidation of Primary Alcohol—Periodic Acid and Chromium Trioxidize

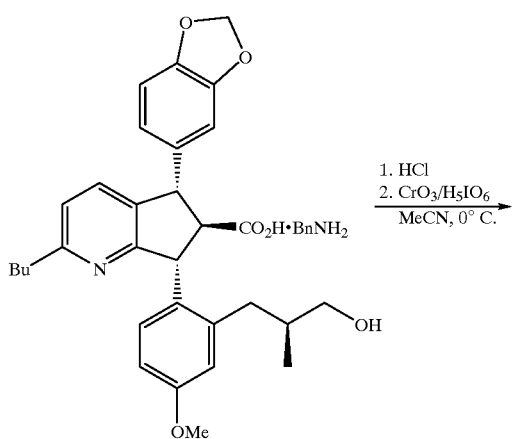

-continued

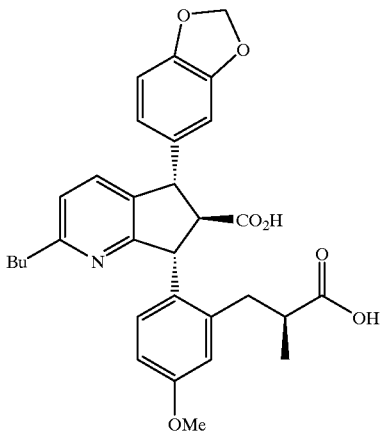

A solution of $H_5IO_6/CrO_3$ is prepared by adding water (1.1 mL) and MeCN to 15.95 g of $H_5IO_6$ to a volume of 160 mL. An aqueous solution of $CrO_3$ (0.16 mL 200 mg/mL) is then added and the mixture is stirred until all the solid dissolved.

A mixture of the benzylamine salt of the hydroxy acid (12.50 g, 20.0 mmol) in MTBE (100 mL) and water (50 mL) is treated with 2.0 N HCl (~10 mL) until pH=3–4. The organic layer is washed with water (3× 50 mL), brine (50 mL) then concentrated to ~30 mL. It is flushed with acetonitrile (100 mL) then diluted with MeCN (to 100 mL). Water (0.75 mL) is then added and the mixture is cooled to −5° C. A portion of the $H_5IO_6/CrO_3$ solution (50 mL, 1.1 molar equiv.) is added in ~5–10 minutes. The remaining portion (110 mL) is added in 30–60 minutes maintaining the batch temperature at −3 to 0° C.

The mixture is aged for 0.5 hour at 0° C. and the completion of the reaction is confirmed by HPLC (<2 A % of the SM). The reaction is quenched with $Na_2HPO_4$ solution (8.52 g in 150 mL $H_2O$), then brine (50 mL). Some inorganic solid remains and is filtered off.

The pH of the aqueous layer should be 3–4. Toluene (150 mL) is added and organic layer is separated and washed with 1:1 brine-water mixture (2×100 mL), then aqueous $NaHSO_3$ (2.15 g uin 50 mL $H_2O$. The organic layer is concentrated to 160 mL to remove most of the acetonitrile (40 mmHg, 30° C. bath).

The mixture is treated with 0.30 N NaOH (150 mL) for 0.5 hour and the organic layer is separated and discarded. MTBE is added (100 mL) to the aqueous layer and the mixture is acidified with 2.0 N HCl (~22.5 mL) to pH=3.5. The organic layer is separated and washed with water (2×50 mL), brine (50 mL) then concentrated to give the crude product as a brown foam.

HPLC conditions: Column: YMC-ODS AM 4.6×250 mm; Solvent: $CH_3CN:H_2O:0.1\ H_3PO_4$ 80:20:0.1 gradient to 100:0:0.1 over 15 min.; Flow rate: 1.0 mL/min.; Temperature: 30° C.; UV detection: 220 nm; RT (hydroxy acid)=5.8 min.; and RT (diacid)=7.8 min.

What is claimed is:

1. A process for preparing a compound of Formula I:

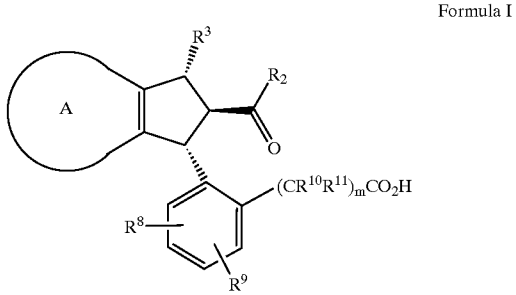

Formula I wherein:

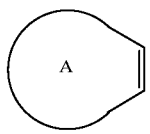

represents:
a) 6-membered heterocyclyl containing one, two or three double bonds, but at least one double bond and 1 heteroatom selected from N, the heterocyclyl is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_3$–$C_8$ cycloalkyl, $CO(CH_2)_nCH_3$, and $CO(CH_2)_nCH_2N(R^5)_2$, $C_1$–$C_8$ alkoxy, $C_1$–$C_8$ alkyl, or $C_3$–$C_8$ cycloalkyl, are unsubstituted one, two or three substituents selected from the group consisting of: OH, $CO_2R^4$, Br, Cl, F, I, $CF_3$, $N(R^5)_2$, $C_1$–$C_8$ alkoxy, $C_3$–$C_8$ cycloalkyl, $CO(CH_2)_nCH_3$, and $CO(CH_2)_nCH_2N(R^5)_2$, aryl is defined as phenyl or naphthyl, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_3$–$C_8$ cycloalkyl, $CO(CH_2)_nCH_3$, $CO(CH_2)_nCH_2N(R^5)_2$, or when aryl is substituted on adjacent carbons they can form a 5- or 6-membered fused ring having one, two or three heteroatoms selected from O, N, and S, this ring is unsubstituted or substituted on carbon or nitrogen with one, two or three substituents selected from the group consisting of: OH, $CO_2R^6$, Br, Cl, F, I, $CF_3$, $N(R^7)_2$, $C_1$–$C_8$ alkoxy, $C_1$–$C_8$ alkyl, $C_3$–$C_8$ cycloalkyl, $CO(CH_2)_nCH_3$, and $CO(CH_2)_nCH_2N(R^5)_2$;

$R^2$ is: $OR^4$ or $N(R^5)_2$;

$R^3$ is:
a) H,
b) $C_1$–$C_8$ alkyl,
c) $C_1$–$C_8$ alkoxyl,
d) $C_3$–$C_7$ cycloalkyl,
e) $S(O)_xR^5$,
f) Br, Cl, F, I,
g) aryl,
h) heteroaryl,
i) $N(R^5)_2$,
j) $NH_2$,
k) —CHO, l) —CO—$C_1$–$C_8$ alkyl,
m) —CO-aryl,
n) —CO-heteroaryl,
o) —$CO_2R^4$, or
p) protected aldehyde;
heteroaryl is defined as a 5- or 6-membered aromatic ring containing 1, 2 or 3 heteroatoms selected from O, N and S, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_3$–$C_8$ cycloalkyl, $CO(CH_2)_n CH_3$, and $CO(CH_2)_n CH_2 N(R^5)_2$,
m is: 2;
n is: 0 to 5;
t is: 0, 1 or 2;
$R^4$ is: H, or $C_1$–$C_8$ alkyl;
$R^5$ is: H, or $C_1$–$C_8$ alkyl, or aryl;
$R^6$, is: H, $C_1$–$C_8$ alkyl, or aryl;
$R^7$ is: H, $C_1$–$C_8$ alkyl, aryl, which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_3$–$C_8$ cycloalkyl, $CO(CH_2)_n CH_3$, $CO(CH_2)_n CH_2 N(R^5)_2$; or when two $R^7$ substutients are on the same nitrogen they can join to form a ring of 3 to 6 atom; and
$R^8$, $R^9$, $R^{10}$ and $R^{11}$ are independently: H, $C_1$–$C_8$ alkyl, $C_2$–$C_8$ alkenyl, $C_2$–$C_8$ alkynyl, $C_1$–$C_8$ alkoxy, $C_1$–$C_8$ alkylthio, aryl, each of which is unsubstituted or substituted with one, two or three substituents selected from the group consisting of: OH, $CO_2R^4$, Br, Cl, F, I, $CF_3$, $N(R^5)_2$, $C_1$–$C_8$ alkoxy, $C_1$–$C_8$ alkyl, $C_2$–$C_8$ alkenyl, $C_2$–$C_8$ alkynyl, $C_3$–$C_8$ cycloalkyl, $CO(CH_2)_n CH_3$, or $CO(CH_2)_n CH_2 N(R^5)_2$;
comprising reacting a compound of Formula II in a solvent, Formula II

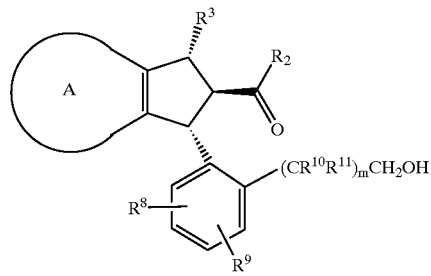

with a solution of periodic acid, a catalytic amount of a chromium reagent in a solvent at a temperature range of about –20° C. to about 40° C. for about 15 minutes to about 24 hours to oxidize to the compound of Formula I.

2. The process as recited in claim 1, wherein the solvent is selected from the group consisting of: acetonitrile, tetrahydrofuran, diethyl ether, MTBE (methyl t-butyl ether), DME (dimethoxyethane), DIGLYME (2-methoxyethyl ether), TRIGLYME (triethylene glycol dimethyl ether), toluene, benzene, hexane, pentane, dioxane, or a mixture of said solvents, including a mixture of said solvents with water.

3. The process as recited in claim 2, wherein the periodic acid ($H_5IO_6$) is utilized in about 2.0 to about 4.0 equivalents.

4. The process as recited in claim 3, wherein the chromium reagent is selected from the group consisting of: $CrO_3$, $Na_2Cr_2O_7$, $K_2Cr_2O_7$, $CrX_3$, where X is Cl, Br, F, $NO_2$, OAc, or $ClO_4$.

5. The process as recited in claim 4, wherein the chromium reagent is utilized in about 0.1 to about 10 mole percent.

6. The process as recited in claim 5, wherein the temperature range is about –20° C. to about 30° C.

7. The process as recited in claim 6, wherein the periodic acid ($H_5IO_6$) is utilized in about 3.5 equivalents.

8. The process as recited in claim 7, wherein the chromium trioxidize ($CrO_3$) is utilized in about 1.0 to about 2.0 mole percent.

9. The process as recited claim 8, wherein the temperature range is about –10° C. to about 0° C.

10. The process as recited in claim 9, wherein the reaction time is about 45 minutes to about 1.5 hours.

11. The process as recited in claim 1, wherein the compound of Formula II is

Formula I

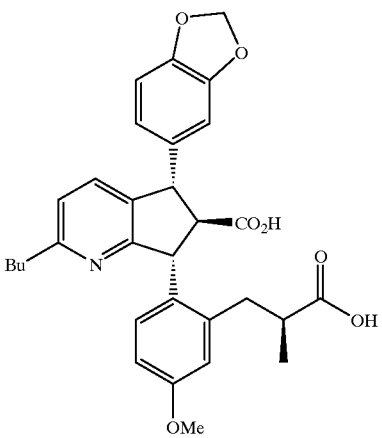

comprising reacting a compound of Formula II in a solvent,

Formula II

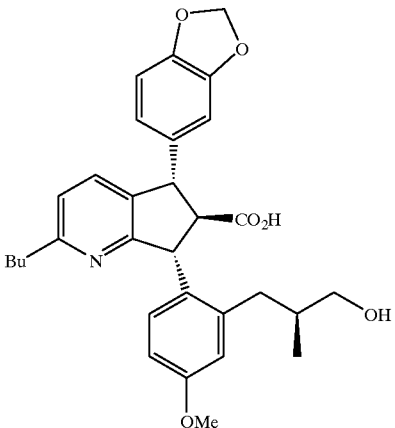

with a solution of periodic acid, a catalytic amount of chromium trioxidize in a solvent at a temperature range of about –20° C. to about 30° C. for about 15 minutes to about 24 hours to oxidize to the compound of Formula I.

12. The process as recited in claim 11, wherein the solvent is acetonitrile and water.

* * * * *